United States Patent
Seeley

(10) Patent No.: US 6,632,268 B2
(45) Date of Patent: Oct. 14, 2003

(54) METHOD AND APPARATUS FOR COMPREHENSIVE TWO-DIMENSIONAL GAS CHROMATOGRAPHY

(75) Inventor: John V. Seeley, Grand Blanc, MI (US)

(73) Assignee: Oakland University, Rochester, MI (US)

(*) Notice: Subject to any disclaimer, the term of this patent is extended or adjusted under 35 U.S.C. 154(b) by 0 days.

(21) Appl. No.: 10/067,378

(22) Filed: Feb. 4, 2002

(65) Prior Publication Data
US 2002/0148353 A1 Oct. 17, 2002

Related U.S. Application Data
(60) Provisional application No. 60/344,077, filed on Dec. 28, 2001, and provisional application No. 60/267,449, filed on Feb. 8, 2001.

(51) Int. Cl.[7] .............................................. B01D 15/08
(52) U.S. Cl. ........................ 95/86; 73/23.39; 96/104
(58) Field of Search .......................... 73/23.35, 23.38, 73/23.39; 95/86, 87; 96/101, 104

(56) References Cited

U.S. PATENT DOCUMENTS

| | | | | |
|---|---|---|---|---|
| 3,865,562 A | * | 2/1975 | Ayers et al. ................... 95/86 |
| 4,204,952 A | * | 5/1980 | Snyder ....................... 210/659 |
| 4,470,832 A | * | 9/1984 | Sugawara et al. ............ 96/103 |
| 5,049,509 A | * | 9/1991 | Szakasits et al. ........... 436/140 |
| 5,135,549 A | * | 8/1992 | Phillips et al. .................... 95/8 |
| 5,196,039 A | | 3/1993 | Phillips et al. |
| 5,236,593 A | * | 8/1993 | Cortes et al. ................ 210/656 |
| 5,281,256 A | * | 1/1994 | Sacks et al. .................... 95/86 |
| 5,376,277 A | * | 12/1994 | Cortes et al. ............... 210/659 |
| 5,398,539 A | * | 3/1995 | Gordon et al. ............. 73/23.35 |
| 5,492,555 A | * | 2/1996 | Strunk et al. ................... 95/86 |
| 5,611,846 A | * | 3/1997 | Overton et al. ............... 96/102 |
| 5,846,292 A | * | 12/1998 | Overton ......................... 95/86 |
| 5,929,321 A | * | 7/1999 | Bertrand .................... 73/23.39 |
| 6,237,396 B1 | * | 5/2001 | Durand et al. ............. 73/23.35 |
| 6,301,952 B1 | * | 10/2001 | De Zeeuw et al. ........ 73/23.35 |
| 6,447,575 B2 | * | 9/2002 | Bremer et al. ................. 95/86 |

OTHER PUBLICATIONS

Helmig, D., et al., Chemosphere 38 2163–2187 (1999).
Phillips, M., et al., Chromatogr. B 729 75–88 (1999).
Liu, Z.Y., et al., J. Chromatogr. Sci 29 227–231 (1991).
Bruckner, C.A., et al., Anal. Chem. 70 2796–2804 (1998).
Frysinger, G.S., et al., J. High Res. Chrom. 22 195–200 (1999).
Kinghorn, R.M., et al., High Res. Chrom. 21 620–622 (1998).

(List continued on next page.)

Primary Examiner—Robert H. Spitzer
(74) Attorney, Agent, or Firm—Ian C. McLeod

(57) ABSTRACT

A two-dimensional gas chromatograph with a primary column (14) and dual secondary columns (26, 28) is described. Flow rates in the primary column are less than those in the secondary columns due to an accumulation valve (16). Typically the ratio of second and third column flow capacities combined to primary column flow capacities between about 10 to 1 and 30 to 1. Volatile organic compounds are detected in environmental samples of air water, soil and in body fluids of animals and humans.

12 Claims, 9 Drawing Sheets

OTHER PUBLICATIONS

Lewis, A. C., et al., Nature 405 778–781 (2000).

Phillips, J.B., et al., J. Chromatogr. A. 856 331–347 (1999).

Bertsch, W., J. High Resol. Chromatogr. 23 167–181 (2000).

Seeley, J. V., et al., Analytical Chem. 72 4346 (2000).

Abraham, M. H., et al., J. Chem. Soc. Perkin Trans. 2 1777 (1994).

Murphy, R.E., et al., Anal. Chem. 70 1585 (1998).

Helmig, D., et al., J. Geophys. Res. 103 22397–22414 (1998).

Woolfenden, E., J. Air Waste Manage. 47 20–36 (1997).

Mathews, J. M., et al., Toxicology and Applied Pharmacology 146 255–260 (1997).

Lin, Y., et al., Clinical Chemistry 41 1028–1032 (1995).

Risby, T. H., et al., Free Radical Biology and Medicine 27 1182–1192 (1999).

Phillips, M., Analytical Biochemistry 247 272–278 (1997).

Roberts, L. J., et al., Free Radical Biology and Medicine 28 505–513 (2000).

Phillips, M., et al., Volatile Organic Compounds in breath as markers of lung cancer: a cross–sectional study, Lancet, 353, 1930–1933 (1999).

* cited by examiner

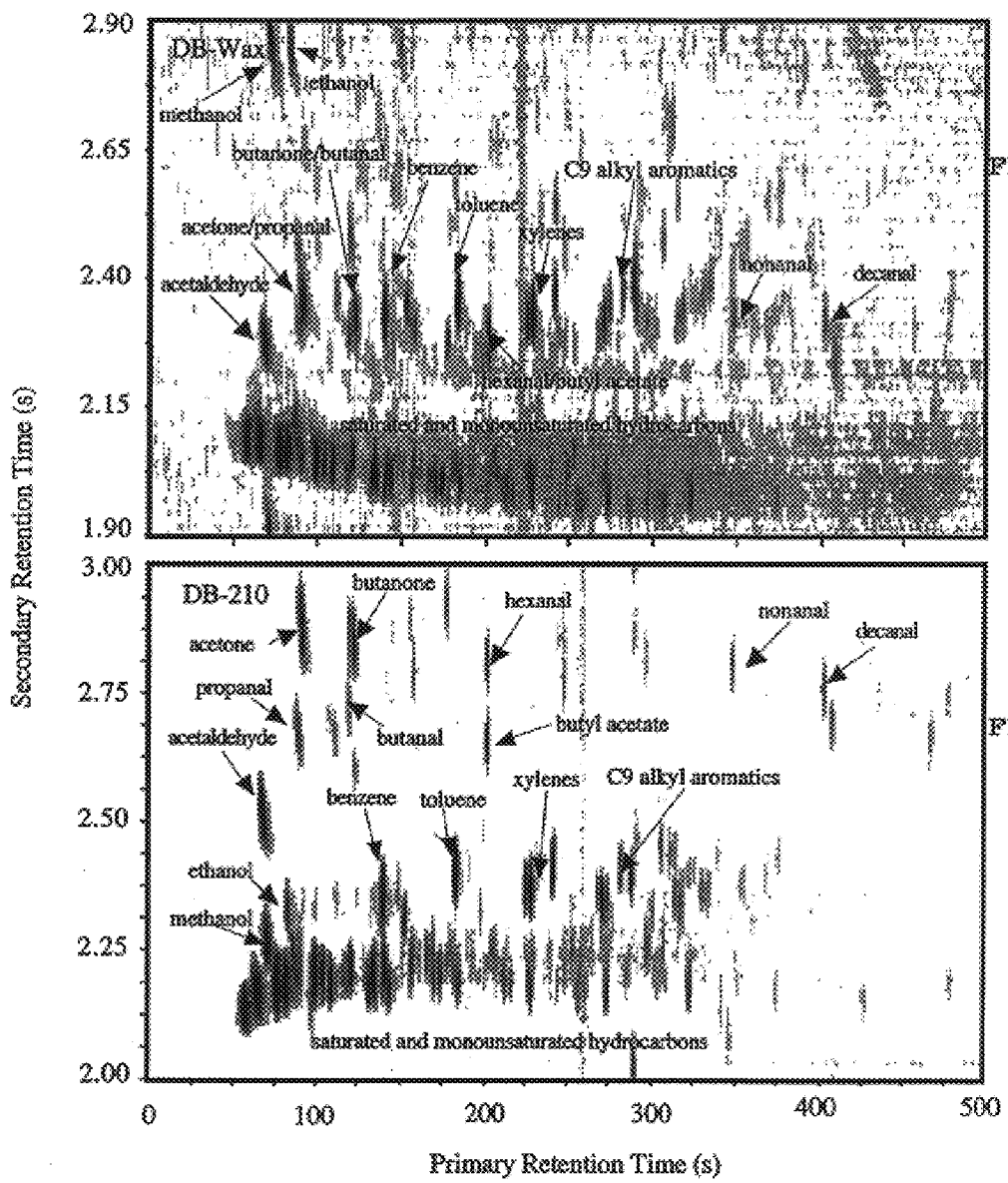

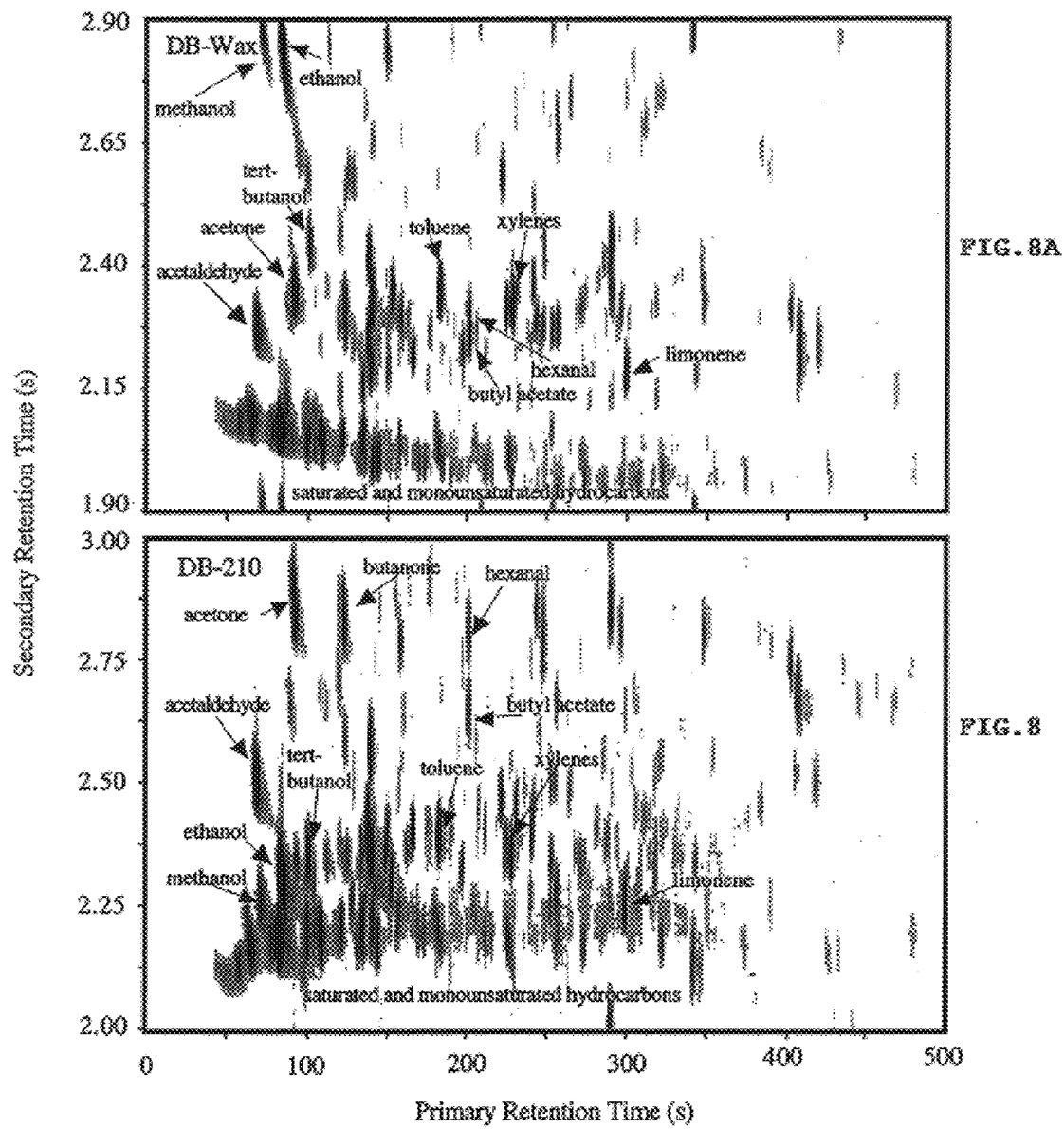

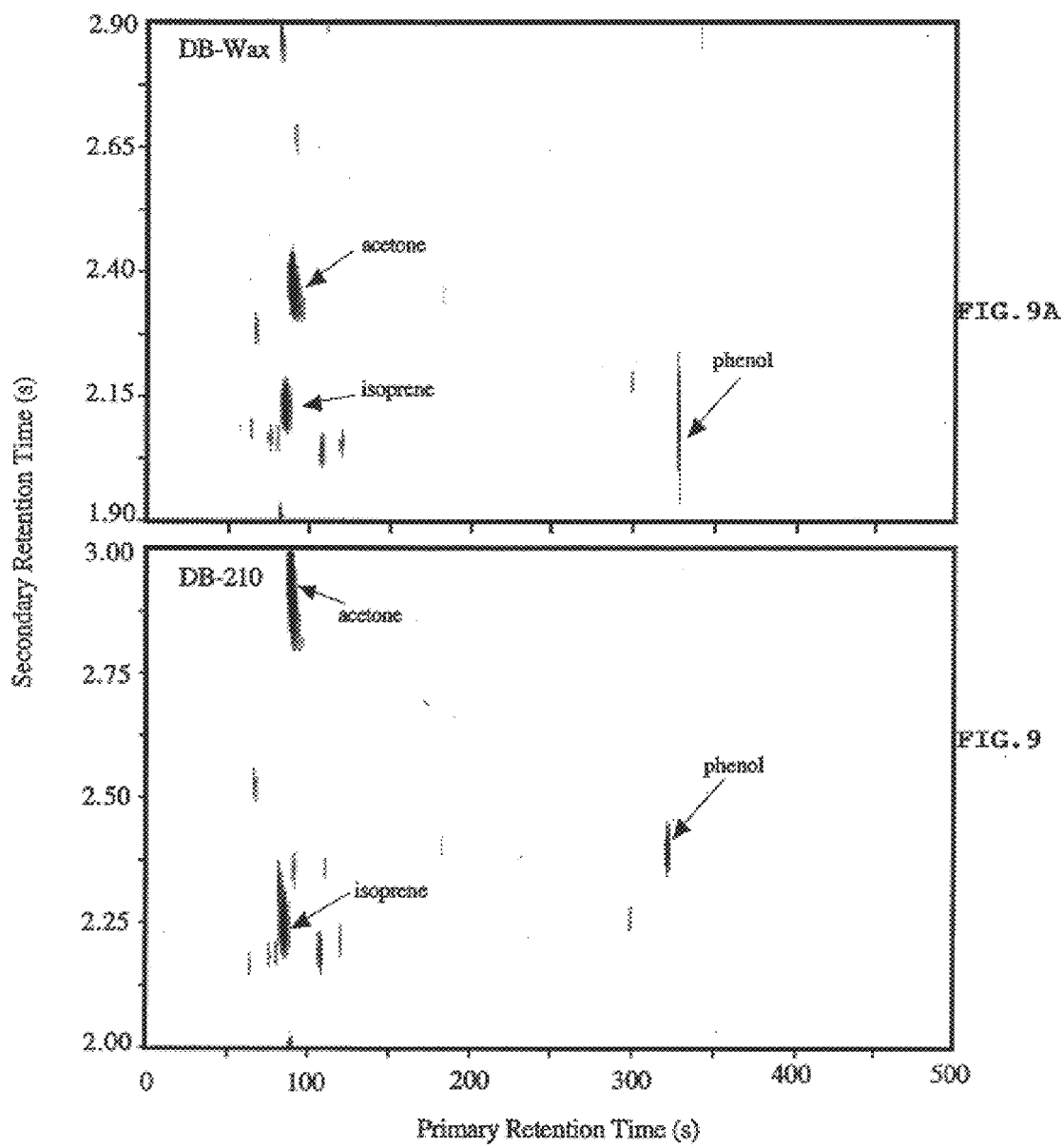

METHOD AND APPARATUS FOR COMPREHENSIVE TWO-DIMENSIONAL GAS CHROMATOGRAPHY

CROSS-REFERENCE TO RELATED APPLICATIONS

This application relies for priority on provisional application Ser. No. 60/267,449, filed Feb. 8, 2001 and provisional application Ser. No. 60/344,077, filed Dec. 28, 2001.

GOVERNMENT RIGHTS

The invention disclosed in this application was supported by the National Science Foundation Grant No. 0094185. The U.S. government has certain rights to this invention.

BACKGROUND OF THE INVENTION (1) Field of the Invention

The present invention relates to a gas chromatographic method and apparatus which uses a primary separation column and parallel secondary separation columns to separate volatile organic compounds (VOCs) in a sample at different times as a result of the sample flowing through the columns. In particular, the present invention relates to a method and apparatus which uses a valve which accumulates a sample from the primary column for transfer to the secondary columns in parallel. The primary column has a smaller fluid flow capacity than the combined fluid capacities of the secondary columns. In this manner, the chromatographic separations of the primary and secondary columns are matched to provide the best available separation of compounds in the sample.

(2) Description of Related Art

Volatile organic compounds (VOCs) are key components in industrial, environmental, and medical samples. Air, water soil, and body fluids often contain hundreds of VOCs (Helmig, D., et al., *Chemosphere* 38 2163–2187 (1999); and Phillips, M., et al., *Chromatogr. B* 729 75–88 (1999)) with concentrations in the part-per-trillion to part-per-million range (Helmig, D., et al., *Chemosphere* 38 2163–2187 (1999); and Phillips, M., et al., *Journal of Chromatography B* 729 75–88 (1999)) Gas chromatography/mass spectrometry (GC/MS) is conventionally used to characterize complex VOC mixtures. However, comprehensive two-dimensional gas chromatography (GC×GC) has recently emerged as an alternative to GC/MS (Liu, Z. Y., et al., *J. Chromatogr. Sci* 29 227–231 (1991); Beens, J., et al., *J. Chromatogr. A* 919 127–132 (2001); Bruckner, C. A., et al., *Anal. Chem.* 70 2796–2804 (1998); Frysinger, G. S., et al., *J. High Res. Chrom.* 22 195–200 (1999); Kinghorn, R. M., et al., High Res. Chrom. 21 620–622 (1998); and Lewis, A. C., et al., *Nature* 405 778–781 (2000)).

GC/MS instruments use gas chromatography to separate mixtures into individual components and mass spectrometry to detect and identify each component. Chromatographic separation is the rate-limiting step: complex samples often require more than 30 minutes to resolve.

Chromatography is an analytical method for the separation and identification of chemical compounds from mixtures. Gas chromatography is a particularly well-known discipline of this science which, when used in combination with quantitative instrumentation (for example GC-IR, GC-UV, GC-MS), provides the user with reliable results. However, in an attempt to find lower cost methods and decrease sample testing time, a variety of sources have taught the technique of comprehensive two-dimensional gas chromatography as a high resolution alternative to the previously known methods. In comprehensive two-dimensional GC, a sample is first injected into and separated by a primary column. Thereafter, at least a portion of the separated sample is collected and injected into a secondary column for further separation.

Comprehensive two-dimensional gas chromatography (GC×GC) is a high resolution alternative to GC/MS. GC×GC has been developed in a limited number of laboratories over the past 10 years (Phillips, J. B., et al., *J. Chromatogr. A.* 856 331–347 (1999); and Bertsch, W., *J. High Resol. Chromatogr.* 23 167–181 (2000)). GC×GC subjects the entire sample to two serial chromatographic separations. The sample is first partially separated by a primary column. Sample components are collected by a modulator as they leave the primary column and are subsequently injected at regular intervals into a secondary column where they undergo a fast secondary separation. The stationary phases of the primary and secondary columns have different selectivities so that species that co-elute from the primary column can be separated by the secondary column. GC×GC frequently produces greater levels of chromatographic separation than GC/MS (Bertsch, W., *J. High Resol. Chromatogr.* 23 167–181 (2000) and Seeley, J. V., et al., Analytical Chem. 72 4346 (2000)).

U.S. Pat. No. 5,196,039 that issued to Phillips et al provides an example of prior art two-dimensional GC. Specifically, Phillips et al disclose a method and apparatus for two-dimensional chromatography wherein a sample is injected and separated in a first column (a first dimension), collected, and then re-injected and separated into a second column (a second dimension) that is in series with the first dimension.

Objects

It is an object of the present invention to provide a comprehensive gas chromatographic method and apparatus which speeds up the time of separation and increases the resolution of a sample. It is further an object of the present invention to provide an apparatus which is relatively economical to assemble and to use compared to prior art methods. These and other objects will become increasingly apparent by reference to the following description and the drawings.

SUMMARY OF THE INVENTION

The present invention relates to a comprehensive two-dimensional gas chromatograph apparatus, said apparatus comprising a primary column, said primary column interacting with a sample to provide a first dimension result; a first secondary column and a second secondary column, said sample interacting with each of said first and second secondary columns to provide a pair of second dimension results; and a valve, said valve providing fluid communication of said sample from said primary column to each said first and second secondary columns, whereby said secondary columns are in a parallel arrangement through a single connection to the valve.

In a preferred embodiment primary column is nonpolar. Further, preferably the first and second secondary columns are polar. Preferably the first secondary column has a selectivity different from second secondary column. Preferably the single connection is through a Y connection with two arms connected to the secondary columns and a leg connected to the valve.

The present invention also relates to a comprehensive two-dimensional gas chromatograph apparatus, said apparatus comprising a primary non-polar column, said primary column interacting with sample to provide a first dimension result; a first polar secondary column and a second polar secondary column, said sample interacting with each of said first and second secondary columns to provide a pair of second dimension results; and a valve, said valve providing fluid communication of said sample from said primary column to each said first and second secondary columns, whereby said secondary columns are in a parallel arrangement through a single connection to the valve.

The primary column has a first flow capacity smaller than the combined second and third flow capacities of the secondary columns and wherein the valve accumulates the sample for transfer to the secondary columns through the single connection to the valve. The ratio of second and third flow capacities combined to primary flow capacity is preferably between about 10 to 1 and 30 to 1. Preferably the ratio of second and third flow capacities to primary flow capacity is about 26.6 to 1. Preferably the primary column has a first flow capacity smaller than the combined second and third flow capacities of the secondary columns and wherein the valve accumulates the sample for transfer to the secondary columns through the single connection to the valve. Preferably the single connection is through a Y connection with two arms connected to the secondary columns and a leg connected to the valve.

The present invention also relates to a method for comprehensive two-dimensional gas chromatography comprising the steps of: injecting a sample into a primary column to obtain a first dimension; communicating said sample from said primary column through a valve; injecting at least a portion of said sample from said valve through a single connection simultaneously into a first and a second secondary column to obtain a pair of second dimensions.

The primary column has a first flow capacity smaller than the combined second and third flow capacities of the secondary columns and wherein the valve accumulates the sample for transfer to the secondary columns through the Y. Preferably the ratio of second and third flow capacities to primary flow capacity is between about 10 to 1 and 30 to 1. Preferably the single connection is through a Y connection with two arms connected to the secondary columns and a leg connected to the valve.

BRIEF DESCRIPTION OF THE DRAWINGS

The present invention may be more fully understood by reference to the accompanying drawings herein where

FIGS. 7 and 7A are 2-D chromatograms from the secondary columns obtained for 3.0 L of air collected in Rochester, Mich. The full-scale intensity of the detector signals is set at 250.

FIGS. 8 and 8A are 2-D chromatograms from the secondary columns obtained for 3.0 L of air collected in the chemical stockroom at Oakland University, Rochester, Mich. The full-scale intensity of the detector signals is set at 500.

FIGS. 9 and 9A are 2-D chromatograms from the secondary columns obtained for 1.5 L of exhaled breath. The full-scale intensity of the detector signals is displayed at 20,000.

DETAILED DESCRIPTION OF THE PREFERRED EMBODIMENTS

Figure 1:
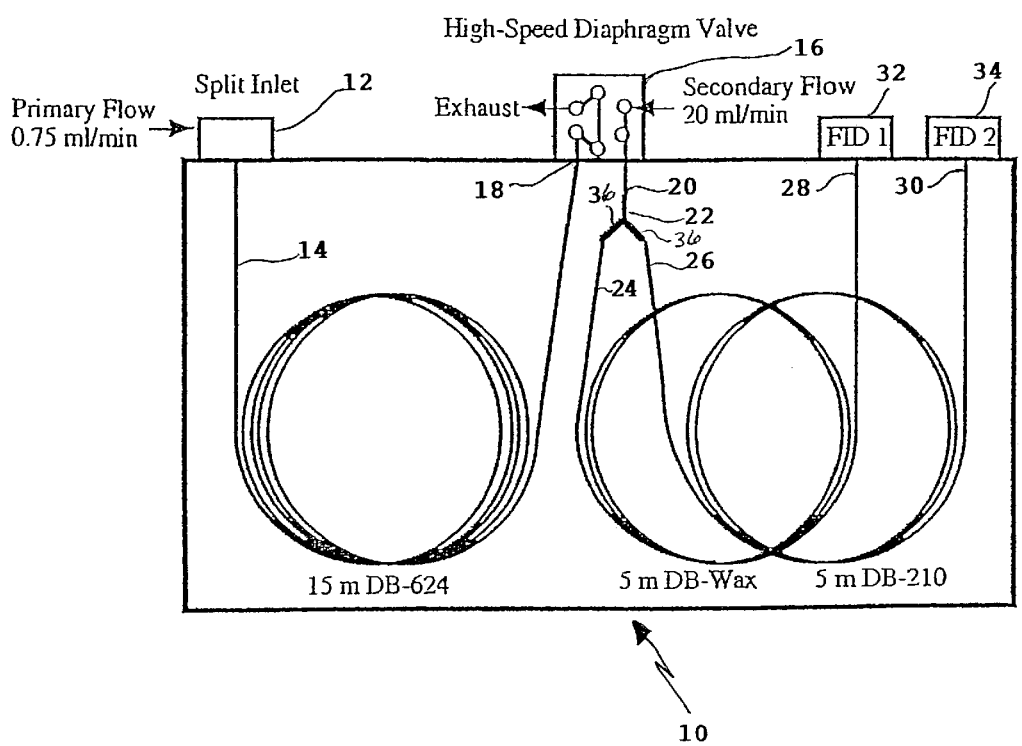
FIG. 1 is a diagrammatic view showing the preferred GC×2GC instrument of the present invention.

Referring now to FIG. 1 there is shown a two-dimensional gas chromatography apparatus having parallel dual secondary columns constructed in accordance with the present invention. Preferably, the apparatus includes an oven 10, an inlet 12 leading to a primary column 14. A valve 16 provides fluid communication between an outlet 18 of the primary column and a secondary inlet 20. The secondary inlet 20 communicates with a Y union 22 having a first 24 and a second 26 secondary column that are arranged in a parallel relationship. Preferably, the outlets 28, 30 of the first 24 and second 26 secondary columns communicate with first 32 and second 34 flame ionization detector.

Still referring to FIG. 1, the inlet 12 to the primary column 14 is a split inlet having a 20:1 split ratio in 0.05 $\mu$L quantities. The primary column 14 is preferably non-polar. For example, in testing, it was found that a 15 m DB-624 capillary column (6% cyanopropylphenyl, 94% dimethyl polysiloxane, 1.4 $\mu$m film thickness), available from J&W Scientific (Folsom, Calif.) was able to perform quite adequately.

The split inlet 12 allows part of the VOC to be vaporized and fed into capillary primary column 14, such that 95% is exhausted from the system and 5% goes to the column 14. The oven 10 heats the sample at an upwards ramping temperature using a heating coil (not shown). This allows for staggered volatilization of the sample. Thus the 20:1 ratio in the Examples. This allows relatively concentrated samples to be tested (10 ppb VOC). Where more dilute VOC are to be tested (i.e. breath samples; 1 ppb VOC) then the ratio can be 1:1, such that 50% is fed to the column 14. The balance is achieved so as to obtain peak widths which are usable and so that there are separations between the peaks as detected by the flame ionization detectors 32 and 34.

The carrier gas for the VOC is usually $H_2$ or He. While $H_2$ can be explosive in air, it is cheaper. In any event, because of the small size of these gases and low viscosity, high diffusion coefficients and flow rates can be maintained.

Preferably, the valve 16 of the apparatus 10 is a high-speed six-port diaphragm valve fitted with a 20 $\mu$L sample loop that collects effluent from the primary column and periodically injects the effluent into the secondary columns as described below. One particular example of a diaphragm valve used in the present invention is available from Valco (Houston, Tex.) (Model No. DV22-2116).

A secondary inlet 20 extends from the valve 16 and terminates at a Y union 22. Extending from each arm 36 of the Y union 22 are the first 24 and second 26 secondary columns. Preferably, these secondary columns are polar and have selectivities that differ between themselves and the primary column. One example particular of suitable first secondary column is a 5 m DB-Wax column (polyethylene glycol, 0.25 μm film thickness) available from J&W Scientific. Likewise, a suitable example of a second secondary column is a 5 m DB-210 column (trifluoropropylmethyl polysiloxane, 0.50 μm film thickness), which is also available from J&W Scientific.

Preferably, each of the secondary columns communicates with a separate flame ionization detector 32, 34. However, other types of detectors are well known in the art and may be easily interchanged with flame detectors 32, 34 of the apparatus 10.

The dual secondary columns 24, 26 of the above-described apparatus 10 permit comprehensive two-dimensional gas chromatography that produces a pair of two-dimensional chromatographs in a single run. Using the above-described apparatus 10, a sample is first injected into the split inlet 12 and communicated into the primary column 14, where it is separated into a first dimension. Preferably, ultra high purity hydrogen is used as a carrier in both the primary 14 and secondary columns. Additionally, the preferred flow of the sample through the primary column is 0.75 ml per minute.

From the primary column 14, the sample enters the diaphragm valve 16 where it is subsequently injected into the secondary inlet 20 and partitioned at the Y union 22 into the parallel secondary columns 24, 26. Notably, the preferred flow of the sample through the secondary columns 24, 26 is 20 ml/min. Effluent from the secondary columns is monitored by a flame ionization detector 32, 34. The use of dual secondary columns increases resolution and qualitative information supplied by traditional comprehensive two-dimensional gas chromatographic analysis. Furthermore, using different secondary columns it should be appreciated that the range, resolution and scope of the present invention may be greatly expanded.

DESCRIPTION OF PREFERRED EMBODIMENTS

Example 1

This Example examines the use of a nonpolar primary column coupled to two polar secondary columns in the instrument of FIG. 1. One secondary column interacts strongly with compounds possessing high levels of hydrogen bond acidity, whereas the other secondary column interacts strongly with dipolar compounds. Differential flow modulation has been used to couple the primary column to the secondary columns. A collection of 130 volatile organic compounds were analyzed using the GC×2GC instrument. The observed secondary retention times form distinct clusters according to the functional groups present and greatly facilitate compound identification. The data demonstrate that the dual secondary column configuration increases separation efficiency for mixtures containing organic compounds with electronegative functional groups (e.g., alcohols, aldehydes, ketones, esters, and oxygen containing compounds).

This example uses the GC×2GC instrument described previously with the six-port diaphragm valve 16 fitted with a sample loop to couple the primary 14 and secondary columns 24 and 26. This technique, called differential flow modulation GC×GC, provides high-speed, high-resolution, and high-sensitivity while maintaining a simple experimental design. Differential flow modulation passes 90% of the effluent exiting the primary column 14 to the secondary columns 24 and 26. Although this is not 100% transfer (like that produced by most thermal modulation systems), the technique is classified as a comprehensive technique because the primary column effluent is sampled throughout a chromatographic run at a frequency (1 Hz) high enough to retain the chromatographic separation produced by the primary column.

Differential flow modulation was used to create a GC×GC instrument that splits the effluent leaving the diaphragm valve 16 into two secondary columns 24 and 26. The resulting technique, dual-secondary column comprehensive two-dimensional gas chromatography (GC×2GC), produces a pair of two-dimensional chromatograms in a single run. This example shows the use of a 6% cyanopropylphenyl, 94% dimethyl polysiloxane primary column coupled to a polyethylene glycol secondary column 24 and a trifluoropropylmethyl polysiloxane secondary column 26. Each column 24 and 26 has a unique selectivity. The primary column 14 interacts largely through dispersive forces, whereas the polyethylene glycol column exhibits strong hydrogen bonding interactions and the trifluoropropylmethyl polysiloxane column exhibits strong dipole—dipole interactions (Li, J., et al., *J. Chromatogr.* 517 103 (1990)). This work evaluates the efficacy of using GC×2GC to analyze complex VOC mixtures.

A Perkin-Elmer (Norwalk, Conn., USA) Autosystem XL gas chromatograph with electronic pneumatics and dual flame-ionization detectors (FIDs) 32 and 34 was used as the experimental platform. Two alterations were made to the gas chromatograph: the 6-port diaphragm valve 16 (described below) was mounted in the location normally reserved for a second sample inlet, and a 100 nF filtering capacitor on each FID electrometer was replaced by an 8 nF capacitor. The filtering capacitor is used for amplification of the peaks. With the 100 nf capacitor, the peak widths are 1 second to 10 seconds. With the nf capacitor, the peak widths are 50 milliseconds wide. In some instances the amplifier capacitor may not be necessary with very low concentration samples.

Neat VOC mixtures were injected into the primary column 14 through a split inlet (20:1 split ratio) in 0.05 μL quantities. The oven temperature in inlet 12 was ramped according to the following program: 40° C. for 0.4 mm, ramp to 60° C. at 40 K min$^{-1}$, ramp to 120° C. at 30 K min$^{-1}$, ramp to 200° C. at 22.5 K min$^{-1}$, hold for 1.0 mm. All capillary columns 14, 24 and 26 were purchased from J & W Scientific (Folsom, Calif., USA). A 15 m×250 μm DB-624 capillary column (6% cyanopropylphenyl, 94% dimethyl polysiloxane, 1.4 μm film thickness) was used as the primary column 14. A 5 m×250 μm DE-Wax column (polyethylene glycol, 0.25 μm film thickness) and a 5 m×250 μm DB-210 column (trifluoropropyl-methyl polysiloxane, 0.50 μm film thickness) were used as the secondary columns 24 and 26. Ultra-high purity hydrogen was used as the carrier gas in the primary and secondary columns. The primary column 14 flow was 0.75 mL min$^{-1}$, and the flow leading to the secondary columns 24 and 26 was 20.0 mL min$^{-1}$. At 40° C., the inlet pressure of the secondary columns was 76 kPA gauge. The high-speed 6-port diaphragm valve 16 (DV22-2116, Valco, Houston, Tex., USA) fitted with a 20 μL sample loop was used to collect effluent from the primary column 14 and periodically inject the effluent into the secondary columns 24 and 26. The valve 16 temperature was maintained at 130° C. Secondary injections were performed at a frequency of 1 Hz; the sample loop in valve 16 was filled with primary column 14 effluent for 0.9 s and flushed for 0.1 s into a short transfer line 20 leading to the secondary columns 24 and 26. The 20.0 mL min$^{-1}$ flow passing through the transfer line 20 was split between the two secondary columns with a fused silica "Y" union 22. Measurements of the flow exiting from each secondary column 24 and 26 indicated that the flow was evenly split to within 2%.

Effluent from each secondary column 24 and 26 was monitored by flame-ionization detectors 32 and 34, respectively. FID signals were monitored at 200 Hz by an Apple Macintosh computer equipped with a data acquisition board and custom software.

A collection of 130 VOCs was divided into 20 simple mixtures, each containing 5 to 10 compounds. The GC×2GC system was used to analyze the mixtures. Each run produced a pair of FID signal arrays that were converted into 2-dimensional chromatograms as previously described (Seeley, J. V., et al., *Anal. Chem.* 72 4346 (2000). Retention times, peak areas and peak widths were determined as previously described (Seeley, J. V., et al., *Anal. Chem.* 72 4346 (2000)) for each 2-dimensional chromatogram using software written in-house. Peaks in the DB-Wax 2-dimensional chromatogram were matched with their respective peaks in the DB-210 2-dimensional chromatogram by correlating primary retention times and peak areas. The observed retention times for the entire set of VOCs are compiled in Table 1.

TABLE 1

Compiled retention times for a collection of volatile organic compounds.

| Compound | Retention Times (s) | | |
|---|---|---|---|
| | DB-624 | DB-Wax | DB-210 |
| Alkanes | | | |
| Methane | 45.3 | 2.06 | 2.09 |
| Pentane | 78.0 | 2.05 | 2.17 |
| Hexane | 106.0 | 2.02 | 2.16 |
| Isooctane | 136.9 | 1.99 | 2.20 |
| Heptane | 139.8 | 1.99 | 2.15 |
| Octane | 175.5 | 1.97 | 2.14 |
| Nonane | 212.6 | 1.97 | 2.15 |
| Decane | 250.6 | 1.96 | 2.15 |
| Undecane | 288.5 | 1.96 | 2.15 |
| Dodecane | 325.7 | 1.95 | 2.14 |
| Tridecane | 361.4 | 1.94 | 2.12 |
| Alkenes and Cyclic Hydrocarbons | | | |
| Isoprene | 83.1 | 2.10 | 2.21 |
| Cyclohexane | 130.6 | 2.04 | 2.20 |
| Cyclohexene | 138.6 | 2.10 | 2.22 |
| Methylcyclohexane | 152.4 | 2.02 | 2.20 |
| 1,7-Octadiene | 172.2 | 2.04 | 2.18 |
| 1-Octene | 174.0 | 2.00 | 2.16 |
| Cyclooctene | 223.7 | 2.13 | 2.27 |
| alpha-Pinene | 234.5 | 2.06 | 2.25 |
| Cyclooctadiene | 237.4 | 2.26 | 2.27 |
| 1-Decene | 249.0 | 2.00 | 2.17 |
| beta Pinene | 254.0 | 2.12 | 2.29 |
| delta 3-Carene | 264.1 | 2.12 | 2.23 |
| Limonene | 271.5 | 2.15 | 2.23 |
| Aromatic Hydrocarbons | | | |
| Benzene | 135.7 | 2.29 | 2.34 |
| Toluene | 174.0 | 2.27 | 2.33 |
| Ethylbenzene | 209.7 | 2.29 | 2.34 |
| p-Xylene | 211.6 | 2.29 | 2.35 |

TABLE 1-continued

Compiled retention times for a collection of volatile organic compounds.

| Compound | Retention Times (s) | | |
|---|---|---|---|
| | DB-624 | DB-Wax | DB-210 |
| m-Xylene | 212.6 | 2.30 | 2.35 |
| o-Xylene | 223.6 | 2.35 | 2.39 |
| Isopropylbenzene | 234.4 | 2.26 | 2.35 |
| n-Propylbenzene | 245.4 | 2.28 | 2.34 |
| 1,3,5-Trimethylbenzene | 250.8 | 2.32 | 2.32 |
| tert-Butylbenzene | 260.6 | 2.25 | 2.36 |
| Isobutylbenzene | 266.6 | 2.24 | 2.35 |
| Butylbenzene | 285.1 | 2.28 | 2.34 |
| Styrene | 224.9 | 2.52 | 2.43 |
| Primary Alcohols | | | |
| Methanol | 65.8 | 2.72 | 2.23 |
| Ethanol | 79.1 | 2.70 | 2.27 |
| 1-Propanol | 108.6 | 2.75 | 2.31 |
| 2-Methyl-1-propanol | 131.2 | 2.67 | 2.33 |
| 1-Butanol | 143.7 | 2.74 | 2.34 |
| 3-Methyl-1-butanol | 169.6 | 2.67 | 2.36 |
| 1-Pentanol | 180.4 | 2.71 | 2.35 |
| 1-Hexanol | 218.0 | 2.74 | 2.39 |
| 1-Heptanol | 256.7 | 2.73 | 2.40 |
| 1-Octanol | 294.8 | 2.69 | 2.39 |
| Secondary Alcohols | | | |
| 2-Propanol | 89.2 | 2.54 | 2.30 |
| 2-Butanol | 120.8 | 2.54 | 2.33 |
| 2-Pentanol | 154.8 | 2.51 | 2.34 |
| 3,3-Dimethyl-2-butanol | 168.7 | 2.40 | 2.35 |
| 4-Methyl-2-pentanol | 176.6 | 2.44 | 2.35 |
| 2-Hexanol | 190.5 | 2.50 | 2.35 |
| 2-Heptanol | 227.9 | 2.51 | 2.38 |
| 2-Octanol | 266.1 | 2.50 | 2.36 |
| 2-Undecanol | 376.7 | 2.42 | 2.34 |
| Tertiary Alcohols | | | |
| 2-Methyl-2-propanol | 96.0 | 2.38 | 2.32 |
| 2-Methyl-2-butanol | 133.5 | 2.38 | 2.35 |
| 2-Methyl-2-pentanol | 165.5 | 2.34 | 2.34 |
| 2-Methyl-2-hexanol | 201.3 | 2.35 | 2.36 |
| Unsaturated and Cyclic Alcohols | | | |
| 2-Methyl-2-propen-1-ol | 139.9 | 3.13 | 2.32 |
| 4-Penten-1-ol | 178.3 | 2.98 | 2.34 |
| cis-3-Hexen-1-ol | 215.9 | 2.94 | 2.41 |
| trans-2-Hexen-1-ol | 218.6 | 2.99 | 2.42 |
| Cyclohexanol | 229.2 | 2.94 | 2.49 |
| 4-Hydroxy-4-methyl-2-pentanone | 218.3 | 2.95 | 3.06 |
| Aldehydes | | | |
| Acetaldehyde | 63.6 | 2.22 | 2.44 |
| Propanal | 86.0 | 2.25 | 2.58 |
| Iso-butanal | 104.5 | 2.20 | 2.63 |
| Butanal | 115.7 | 2.26 | 2.67 |
| Pentanal | 152.2 | 2.25 | 2.69 |
| Hexanal | 189.8 | 2.25 | 2.72 |
| Heptanal | 228.8 | 2.27 | 2.75 |
| Octanal | 268.1 | 2.28 | 2.75 |
| Nonanal | 307.0 | 2.27 | 2.72 |
| Decanal | 344.9 | 2.27 | 2.68 |
| Undecanal | 381.6 | 2.27 | 2.64 |
| Unsaturated Aldehydes | | | |
| Crotonaldehyde | 140.5 | 2.51 | 2.96 |
| trans-2-Hexenal | 216.3 | 2.45 | 3.04 |
| Ketones | | | |
| Propanone | 87.6 | 2.29 | 2.77 |
| Butanone | 118.7 | 2.29 | 2.79 |
| 2-Pentanone | 150.2 | 2.26 | 2.79 |
| 4-Methyl-2-pentanone | 168.7 | 2.21 | 2.78 |
| 2-Hexanone | 187.6 | 2.26 | 2.81 |
| 5-Methyl-2-hexanone | 214.0 | 2.25 | 2.89 |

TABLE 1-continued

Compiled retention times for a collection of volatile organic compounds.

| Compound | Retention Times (s) | | |
|---|---|---|---|
| | DB-624 | DB-Wax | DB-210 |
| 3-Heptanone | 222.9 | 2.24 | 2.74 |
| 2-Heptanone | 225.7 | 2.28 | 2.85 |
| 2-Octanone | 264.6 | 2.29 | 2.84 |
| 2-Nonanone | 303.1 | 2.29 | 2.80 |
| Unsaturated and Cyclic Ketones | | | |
| 5-Hexen-2-one | 183.6 | 2.39 | 2.78 |
| cyclopentanone | 194.4 | 2.57 | 3.06 |
| cyclohexanone | 236.6 | 2.63 | 3.17 |
| Esters | | | |
| Ethyl formate | 89.6 | 2.28 | 2.50 |
| Methyl acetate | 93.5 | 2.27 | 2.52 |
| Vinyl acetate | 108.8 | 2.31 | 2.50 |
| Ethyl acetate | 118.9 | 2.24 | 2.55 |
| Methyl propanoate | 124.5 | 2.25 | 2.51 |
| Isopropyl acetate | 134.6 | 2.17 | 2.54 |
| tert-Butyl acetate | 148.0 | 2.12 | 2.48 |
| Propyl acetate | 153.4 | 2.21 | 2.56 |
| Isobutyl acetate | 175.0 | 2.16 | 2.57 |
| Ethyl butanoate | 184.3 | 2.17 | 2.50 |
| Butyl acetate | 189.5 | 2.21 | 2.57 |
| Methyl pentanoate | 193.4 | 2.22 | 2.52 |
| Isoamyl acetate | 214.0 | 2.20 | 2.62 |
| 4-Penten-1-yl acetate | 224.5 | 2.34 | 2.64 |
| Pentyl acetate | 227.5 | 2.23 | 2.61 |
| Hexyl acetate | 265.1 | 2.24 | 2.59 |
| Octyl acetate | 339.7 | 2.22 | 2.54 |
| Ethers | | | |
| Diethyl ether | 81.5 | 2.09 | 2.22 |
| 1,2-Dimethoxyethane | 132.6 | 2.23 | 2.41 |
| Methylal | 87.2 | 2.15 | 2.32 |
| Furan | 83.8 | 2.27 | 2.28 |
| Oxygenated Aromatics | | | |
| Benzaldehyde | 262.5 | 3.24 | 2.96 |
| Acetophenone | 305.1 | 3.23 | 3.01 |
| Methyl benzoate | 309.3 | 3.00 | 2.73 |
| Phenylacetone | 330.5 | 3.16 | 3.04 |
| Benzyl acetate | 333.8 | 3.05 | 2.73 |
| Ethyl benzoate | 337.4 | 2.83 | 2.70 |
| Cinnamaldeyde | 390.0 | 2.97 | 3.26 |
| Nitriles | | | |
| Acetonitrile | 92.2 | 2.92 | 3.00 |
| Butyronitrile | 152.5 | 2.57 | 3.09 |
| Halogenated Compounds | | | |
| Methylene chloride | 95.9 | 2.50 | 2.28 |
| 2-Chlorobutane | 116.6 | 2.12 | 2.35 |
| Chloroform | 124.7 | 2.53 | 2.25 |
| 1-Chlorobutane | 130.5 | 2.14 | 2.35 |
| 1,1,1-Trichloroethane | 132.3 | 2.19 | 2.23 |
| Trichloroethylene | 148.5 | 2.30 | 2.28 |
| 1,2-Dichloropropane | 152.5 | 2.40 | 2.43 |
| Chloropentane | 167.9 | 2.12 | 2.35 |

The primary retention times are the average of the values obtained from the DB-Wax and DB-210 chromatograms. The two values agreed to within 0.1 s. Most of the compounds had DB-Wax and DB-210 secondary retention times between 1.90 s and 2.90 s. The absolute values of the secondary retention times were verified for a selected set of compounds by changing the secondary injection period from 1 s to 3 s. The unretained retention time was approximately 1.8 s for both secondary columns. Peak areas obtained from the DB-210 chromatogram were consistently 3% larger than the DB-Wax peak areas. Peak widths-at-half-maximum along the primary retention time axis were approximately 1.5 s for all the compounds analyzed. Peak widths along the secondary retention axis were dependent upon the secondary retention times. A linear least-squares fit of the DB-Wax peak widths resulted in the following equation:

$$W_{1/2} = 0.027 t_2 - 0.014 \tag{1}$$

where $W_{1/2}$ is the width-at-half maximum (in seconds) along the secondary retention axis and $t_2$ is the secondary retention time. Thus, poorly retained compounds (e.g., alkanes) had widths of approximately 0.040 s, and highly retained compounds (e.g., 1-alcohols) had widths of approximately 0.060 s. A linear least-squares fit to a plot of the DB-210 peak widths-at-half-maximum resulted in the following equation:

$$W_{1/2} = 0.038 t_2 - 0.036 \tag{2}$$

Poorly retained compounds (e.g., alkanes) had widths of approximately 0.046 s, and highly retained compounds (e.g., 2-ketones) had widths of approximately 0.070 s. The 40% larger broadening rate observed for the DB-210 secondary column is most likely a result of the DB-210 stationary phase being twice as thick as the DB-Wax stationary phase (Gaspar, G., et al., *Anal. Chem.* 50 1512 (1978)).

The method used to transform a one-dimensional signal array into a two-dimensional chromatogram (Seeley, J. V., et al., *Anal. Chem.* 72 4346 (2000)) assumed that all compounds had secondary retention times between 1.90 and 2.90 s. However, several of the VOCs had secondary retention times greater than 2.9 s, but less than 3.9 s. Upon transformation, such compounds appeared as peaks with secondary retention times 1.0 s less (i.e., the secondary injection period) than that their actual value and primary retention times 1.0 s greater than their actual value. Fortunately, the peak width along the secondary retention axis can be used to detect compounds originating from previous injection cycles. For example, methyl benzoate had a primary retention time of 309.3 s, DB-Wax retention time of 3.00 s, and a DB-210 retention time of 2.73 s. Thus, the DB-210 2-dimensional chromatogram had the methyl benzoate peak in the "proper" position because the secondary retention time was between 1.90 and 2.90 s. In contrast, the DB-Wax 2-dimensional chromatogram showed the methyl benzoate peak at a primary retention time of 310.3 s and a secondary retention time of 2.00 s. However, the peak width along the DB-Wax retention time axis was 60% greater than those of nearby peaks. Thus, the peak was determined to be "wrapped-around" from a previous injection cycle, and 1.0 s was added to the secondary retention time and 1.0 s was subtracted from the primary retention time.

Figures 2, 2A:
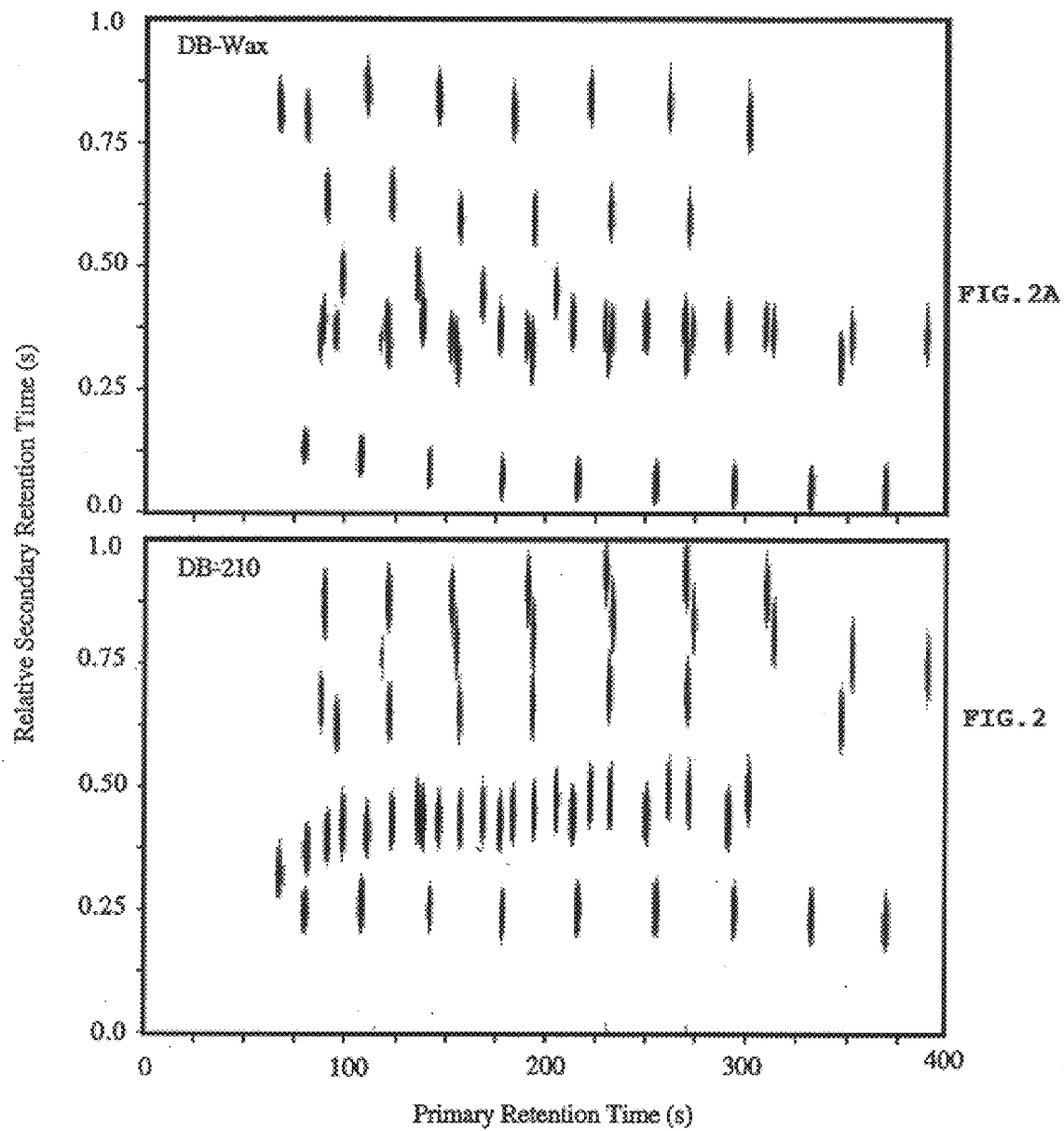
FIGS. 2 and 2A are 2-dimensional chromatograms of a 55-component mixture containing $C_5$–$C_{13}$ alkanes, $C_1$–$C_8$ 1-alcohols, $C_3$–$C_8$ 2-alcohols, $C_4$–$C_7$ 2-methyl-2-alcohols, $C_3$–$C_8$ and $C_{10}$ acetates, $C_3$–$C_{11}$ aldehydes, $C_3$–$C_8$ 2-ketones, and $C_6$–$C_{10}$ alkyl aromatics.
Figures 3, 3A:
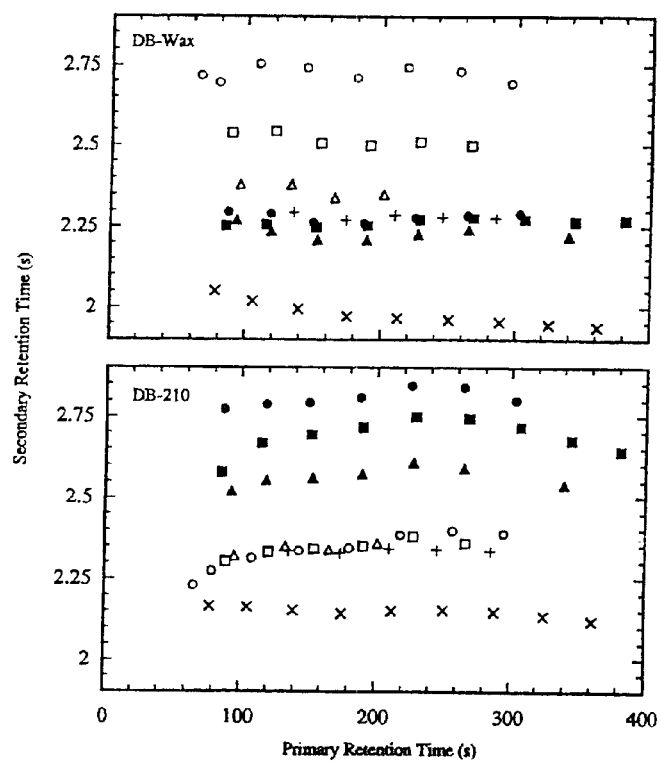
FIGS. 3 and 3A show identities of the chromatographic peaks shown in FIG. 2. The data are organized according to functional group: ○=1-alcohols; □=2-alcohols; △=2-methyl-2-alcohols; ●=2-ketones; ■=aldehydes; ▲=acetates; +=aromatics; x=alkanes. Compounds within each functional class differ only by the length of their straight-chain alkyl group.

To demonstrate the performance of the GCx2GC system, several mixtures were combined to produce a 55-component sample containing the following compounds: $C_5$–$C_{13}$ n-alkanes, $C_1$–$C_8$ 1-alcohols, $C_3$–$C_8$ 2-alcohols, $C_4$–$C_7$ 2-methyl-2-alcohols, $C_3$–$C_8$ and $C_{10}$ acetates, $C_3$–$C_{11}$ aldehydes, $C_3$–$C_8$ 2-ketones, and $C_6$–$C_{10}$ alkyl aromatics. Compounds within each functional class (e.g., alkanes, 1-alcohols, etc.) differed only by the length of their straight-chain alkyl group. The chromatogram for this mixture is shown in FIG. 2. The data are also represented in FIG. 3 as two-dimensional scatter plots organized according to functional group. FIG. 2 and FIG. 3 demonstrate the complementary nature of the DB-Wax and DB-210 secondary columns for analyzing the 55-component mixture: The DB-Wax 2-dimensional chromatogram easily distinguishes the alkanes, primary alcohols, secondary alcohols, and tertiary alcohols, but the aldehydes, ketones, acetates, and aromatic compounds all display similar secondary retention times. The DB-210 2-dimensional chromatogram easily distinguishes the alkanes, acetates, aldehydes, and ketones, but the primary, secondary, and tertiary alcohols, and aromatic compounds display similar secondary retention times.

Figure 4:
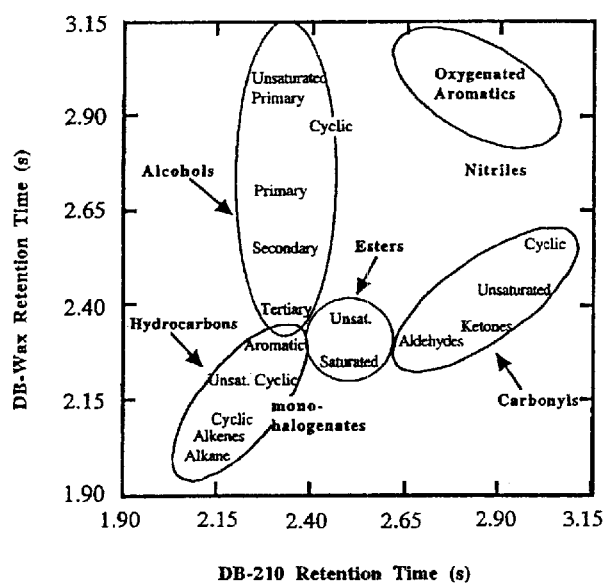
FIG. 4 is a graph showing the approximate clustering of secondary retention times observed for several functional group classes.

The approximate secondary retention times observed for a wide variety of compound classes is shown in FIG. 4. Compounds that are nonpolar and not highly polarizable (e.g., alkanes, monounsaturated hydrocarbons, and saturated cyclic hydrocarbons) have minimal retention on both columns. Highly polarizable compounds having neither large dipole moments nor hydrogen bonding functional groups (e.g., dienes, unsaturated cyclic hydrocarbons, and aromatic compounds) display moderate retention on both secondary columns. Compounds with high levels of hydrogen bond acidity but moderate dipole moments (e.g., primary and secondary alcohols) have high retention on the DB-Wax column and moderate retention on the DB-210 column. Compounds with large dipole moments but with low hydrogen bond acidity (e.g., ketones and aldehydes) display high retention on the DB-210 column and moderate retention on the DB-Wax column. High levels of retention is observed on both secondary columns for compounds that are both highly polarizable and have large dipole moments (e.g, oxygenated aromatics). All of these observations are in agreement with the established selectivities of the DB-624, DB-Wax, and DB-210 stationary phases (Li, J., eta l., *J. Chromatogr.* 517 103 (1990)).

Figure 5:
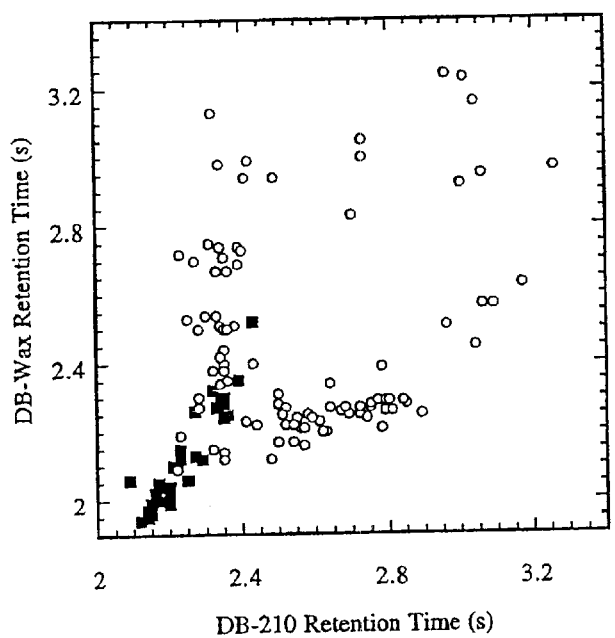
FIG. 5 is a graph showing DB-Wax retention time for 130 VOCs plotted as a function of DB-210 retention time. The compounds have been placed into two categories: hydrocarbons (■) and compounds with electronegative atoms (○).

FIG. 5 is a scatter plot of the secondary retention times obtained for the 130 VOCs. The compounds have been categorized as either hydrocarbons or compounds containing one or more electronegative atoms (O, N, or Cl). Hydrocarbons have DB-210 secondary retention times that are highly correlated with their DB-Wax retention times. A linear fit to the hydrocarbon data produces a correlation coefficient of 0.942, indicating that any separation or qualitative information provided by the DB-210 column is largely redundant with that produced by the DB-Wax column. This is not surprising, as the retention of hydrocarbons on standard liquid stationary phases is primarily dictated by size and polarizability, and not by hydrogen bonding or dipole—dipole interactions (Abraham, M. H., et al., *J. Chem. Soc. Perkin Trans.* 2 1777 (1994)). Thus, the data generated by the dual secondary column configuration should aid in the identification of VOCs containing electronegative functional groups.

The measured retention times and peak widths were used to compare the separation efficiency of single-column GC analysis, GCxGC analysis, and GCx2GC analysis for the compounds and conditions of this study. A pair of compounds was classified as unresolved by the primary column if the calculated value of primary column resolution was less than 1.0. Primary column resolution, $R_1$, was calculated (Giddings, J. C., *Unified Separation Science.* J. Wiley New York (1991)) by $$R_1 = 0.59 \frac{\Delta t_1}{\langle w_{1/2} \rangle_1} \quad (3)$$

where $\Delta t_1$ is the difference in tabulated primary retention times, and $\langle w_{1/2} \rangle_1$ is the average peak width-at-half maximum along the primary retention time axis. A primary peak width-at-half maximum of 1.5 s was assumed for all of the compounds. The VOC data indicate that 174 of the 8385 possible pairs of compounds have a primary resolution less than 1.0. In addition, 112 of the 130 compounds are members of at least one of the 174 overlapping pairs. Thus, if all 130 VOCs were injected into the primary column at the same time, only 18 compounds would be expected to be fully resolved at the exit of the DB-624 column.

A pair of compounds was classified as unresolved by GCxGC analysis if the calculated value of two-dimensional resolution was less than 1.0. The DB-624/DB-Wax data and DB-624/DB-210 data were analyzed separately. The two-dimensional resolution, $R_2$, was calculated (Murphy, R. E., et al., *Anal. Chem.* 70 1585 (1998)) by $$R_2 = 0.59 \sqrt{\left(\frac{\Delta t_1}{\langle w_{1/2} \rangle_1}\right)^2 + \left(\frac{\Delta t_2}{\langle w_{1/2} \rangle_2}\right)^2} \quad (4)$$

where $\Delta t_2$ is the difference in secondary retention times, and $\langle w_{1/2} \rangle_2$ is the average width-at-half maximum along the secondary retention axis. Equations (1) and (2) were used to calculate secondary peak widths for the DB-624/DB-Wax configuration and DB-624/DB-210 configuration, respectively. Compounds with a secondary retention time greater than 2.9 s had 1.0 s added to their primary retention time and 1.0 s subtracted from their secondary retention time, thus placing the peak in the experimentally observed position. For the DB-624/DB-Wax configuration, 34 of the 8385 possible compound pairs produce overlapping peaks and 46 of the 130 compounds are members of at least one overlapping pair. Thus, if all 130 VOCs were injected at the same time, 84 compounds would be predicted to be resolved in the DB-624/DB-Wax chromatogram. For the DB-624/DB-210 configuration, 29 of the 8385 possible pairs produce overlapping peaks and 45 of the 130 compounds are members of at least one overlapping pair. Thus, if all 130 VOCs were injected at the same time, 85 compounds would be predicted to be resolved in the DB-624/DB-210 chromatogram.

Compounds were classified as unresolved by GCx2GC analysis if they were unresolved in both two-dimensional chromatograms. Under this assumption, only 6 of the 8385 possible pairs are unresolved. When considering mixtures with more than two compounds, it is important to note that the interfering compounds need not be the same. For example, compound A can be pair-wise resolved by GCx2GC with both compound B and compound C, but be unresolved when a mixture of A, B, and C is examined. This is possible if A overlaps with B in one chromatogram and A overlaps with C in the other chromatogram. The simulation results show that 21 of the 130 compounds are members of overlapping pairs in both column configurations. Thus, if all 130 VOCs were injected at the same time, 109 compounds would be predicted to be resolved by GCx2GC analysis (i.e., the number of unresolved compounds decreases by a factor of two when going from GCxGC analysis to GCx2GC analysis). These results indicate that in addition to increased qualitative information, GCx2GC analysis can increase separation efficiency.

The results demonstrate that dual secondary columns can increase the resolution and qualitative information supplied by comprehensive two-dimensional gas chromatographic analysis. The largest improvement in performance is expected for mixtures containing compounds with a wide range of dipole moments and hydrogen bond acidities. Thus, our GCx2GC configuration is well suited for analyzing samples containing oxidized or halogenated compounds (such as environmental and biomedical samples) (Helmig, D., et al., *Chemosphere* 38 2163 (1999); Phillips, M., et al., *J. Chromatogr. B* 729 75 (1999); and Helmig, J., et al., *J. Geophys. Res.* 103 22 (1998)), but not as useful for samples dominated by hydrocarbons (such as most petrochemical samples). It is possible that other column configurations can be developed to extend the scope of GC×2GC analysis.

TABLE 2

Results of the Overlap Simulations

| Instrument Configuration | Overlapping Pairs[a] | Unresolved Compound[b] |
|---|---|---|
| GC | 174 | 112 |
| GC × GC DB-Wax | 39 | 48 |
| GC × GC DB-210 | 38 | 56 |
| GC × 2GC | 8 | 28 |

[a]Number of unresolved pairs when all possible 2-component combinations of the 130 VOCs are analyzed sequentially (8385 different pairs).
[b]Number of unresolved compounds when the 130 VOCs are analyzed simultaneously.

Example 2

In the following Example the comprehensive two-dimensional gas chromatograph with dual secondary columns (GC×2GC) as shown in FIG. 1 was used to characterize gaseous mixtures of volatile organic compounds (VOCs). Samples were collected on multi-layer sorbent tubes and introduced into the gas chromatograph using a thermal desorption apparatus. Differential flow modulation by sample accumulation was used to couple the primary column 14 to the secondary columns 24 and 26. Each GC×2GC analysis produced a pair of two-dimensional gas chromatograms. The chromatograms provided complementary information due to the unique selectivities of the secondary columns. The additional information was especially useful in separating and identifying oxygenated and aromatic compounds. Samples of outdoor air, indoor air, and exhaled breath were analyzed with the GC×2GC system. More than 100 volatile organic compounds could be separated in less than 10 minutes. The identities of approximately 50 peaks were determined for each sample.

The following example examined the use of a non-polar primary column, a polyethylene glycol secondary column, and a trifluoropropylmethyl polysiloxane secondary column. Each column has a unique selectivity. The primary column interacts largely through dispersive forces, the polyethylene glycol column exhibits strong hydrogen bonding interactions, and the trifluoropropylmethyl polysiloxane column exhibits strong dipole—dipole interactions (Li, J. J., et al., *J. Chromatogr.* 517 103 (1990)). Mixtures containing compounds with a wide range of dipole moments and hydrogen bond acidities such as alcohols, ketones, and chlorinated compounds were separated.

The GC×2GC of FIG. 1 was used to analyze indoor air, outdoor air, and exhaled breath. Such samples are known to contain numerous VOCs with a wide variety of functional groups (Helmig, D., et al., *Chemosphere* 38 2163–2187 (1999); Phillips, M., et al., *J. Chromatogr. B* 729 75–88 (1999); Lewis, A. C., et al., *Nature* 405 778–781 (2000); and Helmig, D., et al., *J. Geophys. Res.* 103 22397–22414 (1998)).

The oven temperature was ramped according to the following program: 40° C. for 0.50 min, ramp to 95° C. at 33° C. min$^{-1}$, ramp to 140° C. at 23.7° C. min$^{-1}$, ramp to 200° C. at 16.5° C. min$^{-1}$, hold for 1.00 mm. All capillary columns were purchased from J&W Scientific. The primary column 14 was a 15 m×250 μm DB-624 capillary column (6% cyanopropylphenyl, 94% dimethyl polysiloxane, 1.4 μm film thickness). The secondary columns 24 and 26 were a 5 m×250 μm DB-Wax capillary column (polyethylene glycol, 0.25 μm film thickness) and a 5 in×250 μm DB-210 capillary column (trifluoropropylmethyl polysiloxane, 0.50 μm film thickness). Ultra-high purity hydrogen was used as the carrier gas in the primary 14 and secondary columns 24 and 26. The primary column 14 flow was approximately 0.75 ml min$^{-1}$, and the flow leading to the secondary columns 24 and 26 was 20.0 ml min$^{-1}$. The high-speed 5-port diaphragm valve 16 fitted with a 20 μL sample loop was used to collect effluent from the primary column and periodically inject it into the secondary columns. Secondary injections were performed at a frequency of 1 Hz: the sample loop was filled with primary column 14 effluent for 0.9 s and flushed for 0.1 s into a short transfer line leading to the secondary columns 24 and 26. The 20.0 ml min$^{-1}$ flow passing through the transfer line 30 was split between the two secondary columns 24 and 26 with a fused silica "Y" union 22. Effluent from each secondary column 24 and 26 was monitored by a flame-ionization detector.

Gaseous samples were collected on multi-layer sorbent tubes containing 200 mg of Carbotrap C, 200 mg of Carbotrap, and 100 mg Carbosieve adsorbents. Similar sampling tubes have been shown to effectively trap VOCs within the volatility range of $C_3$–$C_{15}$ alkanes (Helmig, D., et al., *J. Geophys. Res.* 103 22397–22414 (1998)). Gaseous VOCs were collected by drawing air through sorbent tubes at 100 ml min$^{-1}$. Sorbent tubes were heated to 45° C. during sampling to reduce water accumulation. Air samples were drawn directly through the tubes for 30 min. Exhaled breath samples were collected in 2-L tedlar bags, then drawn through the sorbent tubes for 15 min. VOCs collected on the sorbent tubes were injected into the GC×2GC system with a Perkin-Elmer ATD 400 thermal desorption unit. The split flows on the ATD were adjusted such that 33% of the desorbed VOCs were transferred to the GC×2GC system.

The quantitative performance of the ATD/GC×2GC system was evaluated by analyzing sorbent tubes containing known amounts of toluene. A dilution system containing a toluene permeation tube was used to make gaseous standards. Seven sorbent tubes were loaded with 3.0 ng to 10.0 ng of toluene. The tubes were analyzed with the ATD/GC×2GC system. Peak areas determined from the DB-210 chromatogram were consistently 3% larger than the areas determined from the DB-Wax chromatogram. A plot of toluene peak area versus the mass of toluene displayed an excellent linear correlation ($R^2$=0.999). A 0.3 ng detection limit for toluene was calculated from the regression parameters (Felinger, A., *Data Analysis and Signal Processing in Chromatography*, Elsevier: Amsterdam (1998)). Thus, it was estimated that the ATD/GC×2GC system can detect toluene at concentrations down to approximately 20 parts-per-trillion when 3.0 L of air is sampled. This experiment was repeated for hexane, and similar results were observed. The reproducibility of the ATD/GC×2GC system was tested by analyzing six different sorbent tubes loaded with 6.0 ng of toluene. The area of the resulting toluene peaks had a relative standard deviation of 3%. This RSD is similar to values previously reported for conventional GC/FID analysis of air samples collected on sorbent tubes (Woolfenden, E., *J. Air Waste Manage.* 47 20–36 (1997)).

Figure 6:
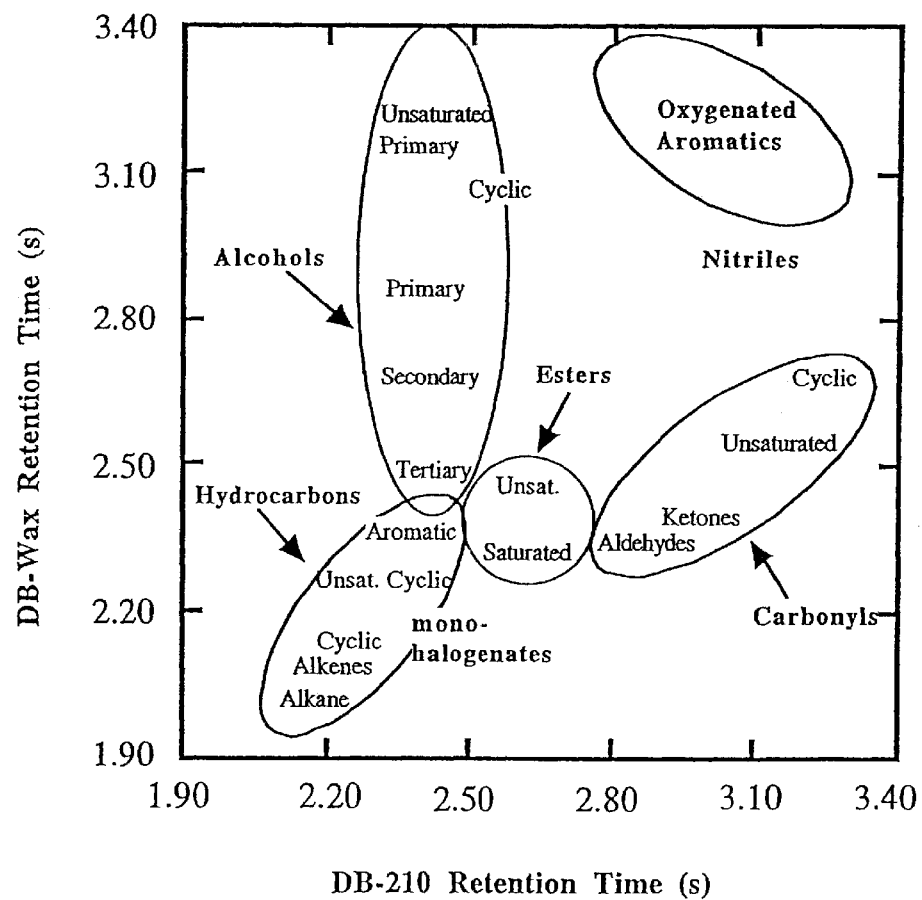
FIG. 6 is a graph showing secondary retention times observed for several functional group classes.

The GC×2GC retention times of over 150 volatile organic compounds were determined. As expected, primary retention is largely determined by compound size, whereas secondary retention times are dictated by functional group. The secondary retention times observed with the ATD/GC×2GC for several functional group classes are shown in FIG. 6. The DB-Wax secondary column displays high levels of retention for compounds with large hydrogen bonding acidities (such as alcohols) and the DB-210 column displays high levels of retention for compounds with large dipole moments (such as carbonyls). The dual secondary column configuration is particularly well suited for differentiating oxygenated compounds and aromatic compounds: Ketones, aldehydes, esters, and aromatics all have similar secondary retention on the DB-Wax column, but vastly different retention on the DB-210 column. In contrast, primary alcohols, secondary alcohols, tertiary alcohols, and aromatics have similar DB-210 retention but vastly different DB-Wax retention times. All of these compound classes are known to be important constituents in air and in breath (Phillips, M., et al., *J. Chromatogra. B* 729 75–88 (1999); and Helmig, D., et al., *J. Geophys. Res.* 103 22397–22414 (1998)). Table 2 contains a list of compounds that have been identified in our outdoor air, indoor air, and breath chromatograms.

FIG. 7 contains a set of 2-D chromatograms typical of those obtained for outdoor air in suburban and rural locations. The chromatograms are displayed with a full-scale signal intensity of 250 (arbitrary units). The peaks with greatest intensity appear to be elongated because they are off-scale for the chosen plotting parameters (e.g., toluene has a maximum peak height of 900 but the full-scale signal intensity is 250). Over 80 peaks are observed in each chromatogram. Several of the major peaks are labeled in FIG. 7. The largest peaks represent compounds with concentrations near 1 part-per-billion. The main VOCs present are saturated hydrocarbons, aromatic hydrocarbons, ketones, and aldehydes. The DB-Wax 2-D chromatogram produces a distinct band of peaks with secondary retention times near 2.0 s. These peaks originate from saturated and monounsaturated hydrocarbons with carbon numbers ranging from 4 to 14. A second peak band is observed at a secondary retention time of approximately 2.35 s. These peaks originate from aromatic hydrocarbons, saturated ketones, and saturated aldehydes. The DB-210 chromatogram produces a distinct band of saturated and monounsaturated hydrocarbon peaks with low secondary retention (approximately 2.15 s). In contrast to the DB-Wax chromatogram, the aromatic hydrocarbons, ketones, and aldehydes have significantly different secondary retention times in the DB-210 chromatogram. Thus, several sets of compounds that overlap in the DB-Wax chromatogram can be fully resolved in the DB-210 chromatogram (e.g., acetone and propanol).

FIG. 8 contains a set of 2-D chromatograms obtained from air in the chemical stockroom at Oakland University, Rochester, Mich. The full-scale intensity is 500. As expected, the chromatograms contain a multitude of high intensity peaks. The GC×2GC system can fully separate over 100 peaks; however, some regions of the chromatogram are particularly congested (such as near a primary retention time of 140 s).

Figures 10, 10A:
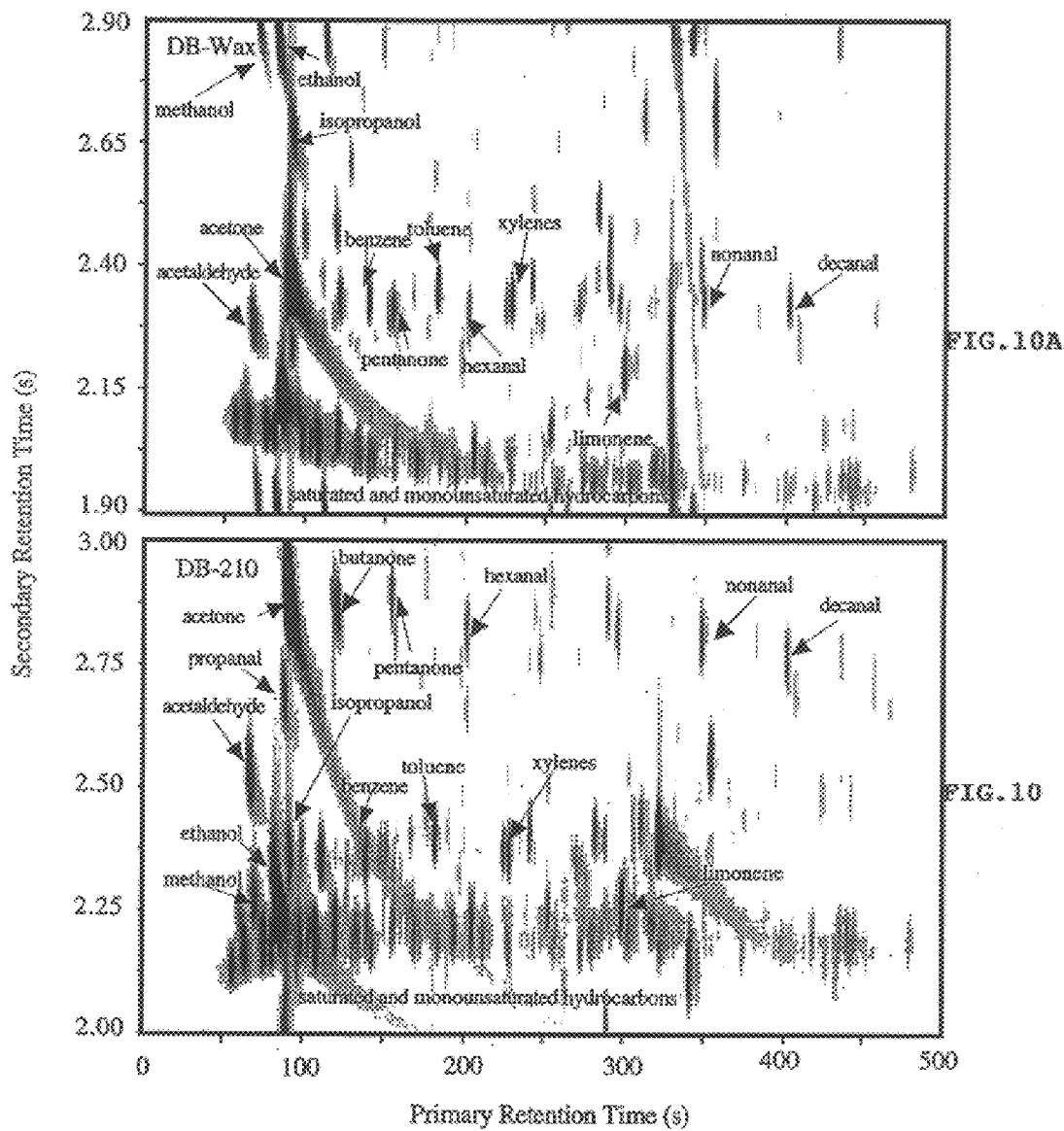
FIGS. 10 and 10A are 2-D chromatograms obtained for 1.5 L of exhaled breath. The full-scale intensity of the detector signals is displayed at 500.

FIG. 9 contains a set of 2-D chromatograms obtained from the breath of a healthy non-smoking individual. The full-scale signal intensity is 20,000 (i.e., a factor of 20 greater than that of FIG. 3). Acetone and isoprene were observed in quantities greater than 20 ppb and produced off-scale peaks. Phenol was observed at a primary retention time of 321 s. This compound is highly retained by the DB-Wax column (8.06 secondary retention time). In fact the peak is wrapped-around from several previous secondary injection cycles. In contrast, phenol is only moderately retained by the DB-210 column (2.40 s secondary retention time). FIG. 10 contains the same chromatograms shown in FIG. 9, but with a full-scale signal intensity of 500. Nearly 100 peaks are fully resolved in the breath chromatograms.

The ability of the DB-Wax column to separate alcohols is demonstrated in the clear distinction of methanol, ethanol, and isopropanol, whereas the DB-210 column is useful at separating the numerous ketones and aldehydes found in breath.

The results indicate that GC×2GC is particularly useful in characterizing the VOCs found in indoor air, outdoor air, and breath. It is important to note that the separations described here were performed in approximately 15% of the time normally required to analyze similar samples with GC/MS (Phillips, M., et al., *J. Chromatogr. B* 729 75–88 (1999); and Helmig, D., et al., *J. Geophys. Res.* 103 22397–22414 (1998)).

TABLE 3

Compounds identified in the analysis of outdoor air, indoor air and breath.

| compound | Retention times (s) | | | Samples Observed |
|---|---|---|---|---|
| | DB-624 | DB-Wax | DB-210 | |
| acetaldehyde | 66 | 2.29 | 2.52 | i, o, b |
| methanol | 69 | 2.90 | 2.27 | i, o, b |
| isopentane | 76 | 2.07 | 2.19 | i, o, b |
| pentane | 79 | 2.07 | 2.19 | i, o, b |
| ethanol | 82 | 2.85 | 2.33 | i, o, b |
| isoprene | 84 | 2.13 | 2.25 | o, b |
| propanal | 87 | 2.32 | 2.67 | i, o, b |
| 2-propanol | 90 | 2.67 | 2.36 | i, o, b |
| acetone | 90 | 2.35 | 2.88 | i, o, b |
| tert-butanol | 99 | 2.45 | 2.36 | i, b |
| hexane | 107 | 2.04 | 2.19 | i, o, b |
| methacrolein | 109 | 2.38 | 2.68 | i, o, b |
| 1-propanol | 110 | 2.90 | 2.36 | i, o, b |
| butanal | 116 | 2.30 | 2.74 | i, o, b |
| methyl vinyl ketone | 117 | 2.48 | 2.87 | i, o, b |
| butanone | 120 | 2.34 | 2.87 | i, o, b |
| ethyl acetate | 121 | 2.27 | 2.60 | i, o |
| benzene | 138 | 2.33 | 2.37 | i, o, b |
| isopropyl acetate | 138 | 2.20 | 2.58 | l |
| isooctane | 139 | 2.01 | 2.21 | i, o, b |
| 1-butanol | 147 | 2.85 | 2.37 | i, o, b |
| 2-pentanone | 153 | 2.32 | 2.90 | i, b |
| pentanal | 156 | 2.31 | 2.80 | i, o, b |
| 4-methyl-2-pentanone | 175 | 2.28 | 2.92 | i, o, b |
| toluene | 181 | 2.36 | 2.41 | i, o, b |
| octane | 183 | 2.01 | 2.20 | i, o, b |
| butyl acetate | 200 | 2.26 | 2.66 | i, o, b |
| hexanal | 200 | 2.31 | 2.82 | i, o, b |
| ethylbenzene | 223 | 2.33 | 2.37 | i, o, b |
| nonane | 227 | 1.99 | 2.17 | i, o, b |
| m,p-xylene | 227 | 2.34 | 2.38 | i, o, b |
| o-xylene | 240 | 2.38 | 2.42 | i, o, b |
| heptanal | 246 | 2.29 | 2.76 | i, o, b |
| alpha-pinene | 252 | 2.07 | 2.26 | i, b |
| n-propyl benzene | 266 | 2.31 | 2.37 | o, b |
| m,p-ethyl toluene | 270 | 2.32 | 2.36 | i, o, b |
| 1,3,5-trimethyl benzene | 273 | 2.36 | 2.35 | i, o, b |
| decane | 273 | 1.98 | 2.18 | i, o, b |
| beta pinene | 276 | 2.14 | 2.32 | b |
| o-ethyl toluene | 280 | 2.37 | 2.42 | i, o, b |
| 1,2,4-trimethyl benzene | 287 | 2.40 | 2.40 | i, o, b |
| benzaldehyde | 288 | 3.28 | 3.03 | l |
| octanal | 294 | 2.32 | 2.82 | i, o, b |
| limonene | 298 | 2.19 | 2.26 | i, b |
| phenol | 321 | 8.06 | 2.40 | b |
| undecane | 322 | 1.98 | 2.18 | i, o, b |
| nonanal | 347 | 2.33 | 2.81 | i, o, b |
| dodecane | 373 | 1.97 | 2.17 | i, o, b |
| decanal | 401 | 2.32 | 2.76 | i, o, b |
| tridecane | 425 | 1.96 | 2.16 | o, b |

*Note: i = indoor air; o = outdoor air; b = breath

Example 4

This Example relates to the application of a dual-secondary column comprehensive two-dimensional gas chromatograph (GC×2GC) of FIG. 1 to quantitate chemical exposure levels. GC×2GC provides high resolution, high sensitivity, and short analysis times for a fraction of the cost of conventional gas chromatography/mass spectrometry techniques. A retention database is developed to allow peaks to be identified under a wide range of chromatographic conditions. Volatile organic compound profiles of breath are obtained with the GC×2GC system. The data is analyzed to determine if this novel technique can be used to detect and quantitate the levels of exposure to cigarette smoke.

VOC levels in breath may also be a sensitive marker for exposure to other hazardous pollutants: Mathews, et al (Mathews, J. M., et al., Toxicology and Applied Pharmacology 146, 255–260 (1997)) have recently shown that rats exposed to trans-1,2-dichloroethylene exhibited greater than 100% increases in breath acetone, hexane, and 2-butanone. Elevated levels were maintained for several hours after exposure. Similar increases in breath VOCs have been observed for individuals exposed to cigarette smoke (Euler, D. E., et al., Clinical Chemistry 42, 303–308 (1996); and Lin, Y., et al., Clinical Chemistry, 41, 1028–1032 (1995)). Lipid peroxidation brought on by oxidant stress has been cited as the cause for increases of VOC production (Risby, T. H., et al., Free Radical Biology and Medicine, 27, 1182–1192 (1999); and Steinberg, F. M., et al., American Journal of Clinical Nutrition, 69, 319–327 (1999)). The non-invasive nature of breath VOC analysis makes it a promising candidate for quantitative exposure assessment. Unfortunately, conventional GC/MS breath analysis is very time consuming; a single breath assay requires the analysis of a breath sample and a room air sample, with each taking approximately 1 hour to complete (Phillips, M., et al., Journal of Chromatography B, 729, 75–88 (1999)). This greatly limits the quantity of samples that can be analyzed.

GC×2GC methods are used for analyzing VOCs in air, water, and breath. In each case, the VOCs are trapped on multi-layer sorbent tubes and then injected into the GC×2GC system of FIG. 1 with a Perkin-Elmer ATD 400 thermal desorption unit. Atmospheric samples are collected by pulling air directly through the sorbent tube. Aqueous samples are analyzed by purging with inert gas and collecting the VOCs in a sorbent tube. Breath samples are collected in Tedlar bags then passed through a sorbent tube.

The data acquisition and analysis software is provided with (Helmig, D., et al., Journal of Geophysical Research, 103, 22397–22414 (1998)) multiple run automation that allows the thermal desorption unit to be loaded with up to 50 samples and run overnight, (Phillips, M., et al., Journal of Chromatography B, 729, 75–88 (1999)) sample data entry that allows sample collection data to be merged with the chromatographic data, and (Phillips, J. B., et al., Journal of Chromatography A, 856, 331–347 (1999)) standardized data output that allows the chromatographic data to be imported into pattern recognition software.

A portable breath collection apparatus (BCA) produced by Menssana Research is used (Phillips, M., Analytical Biochemistry 247, 272–278 (1997)). The BCA was developed by Michael Phillips over the last 10 years and is now being used in clinical studies throughout the United States and Europe. This system allows breath samples to be collected easily. Subjects breathe into the BCA via a disposable mouth piece while the VOCs are trapped in a heated sorbent tube. The BCA is constructed so that alveolar breath is sampled and not dead space breath. After sample acquisition, the sorbent tubes can be stored for weeks without significant artifact formation.

While GC×2GC produces greater separation efficiencies than GC/MS, unknown identification is much more advanced on GC/MS systems. The mass spectrum of an unknown compound can be compared to a library of 100,000 mass spectra. Fully resolved, high-intensity chromatographic peaks can be identified with high levels of confidence. On the other hand, if two components elute simultaneously they produce an overlapped spectrum that results in erroneous matches. Unknown identification in GC×2GC is done by the peak position in the 2 D chromatogram. As GC×2GC is just beginning to be explored, extensive chromatographic libraries do not exist. Conclusive matching requires standard mixtures are analyzed.

Artificial neural networks are used to predict retention times. Neural networks have previously been shown to approximate nonlinear multivariable functions with high accuracy (Gasteiger, J., et al., Angew. Chem. 105, 510 (1993)). Their results indicate that standard 1-dimensional retention time libraries for each of the three columns can be used to predict primary retention time to within 3 s and the secondary retention times to within 0.02 s. This level of accuracy allows a short list of possible matches to be generated for each unknown peak. The neural network/1-D library approach is preferable to simply creating a library of 2-D chromatograms as it can be used to predict retention times under a wide range of experimental conditions (e.g., column dimensions, temperature programs, flow-rates, etc.).

Comprehensive breath measurements of individuals with varying levels of exposure to cigarette smoke are made. Cigarette smoke has been shown to increase breath VOCs through direct exposure to VOCs (Jordan, A., et al., International Journal of mass Spectrometry and Ion Processes, 148, L1–L3 (1995)) and by promoting the endogenous production of VOCs (Lin, Y., et al., Clinical Chemistry 41, 1028–1032 (1995); Risby, T. H., et al., Free Radical Biology and Medicine 27, 1182–1192 (1999); and Steinberg, F. M., et al., American Journal of Clinical Nutrition 69, 319–327 (1999)). Approximately 50 volunteers are recruited from each of the following groups: (1) non-smokers who live and work in essentially smoke-free environments, (2) heavy smokers who smoke over 20 cigarettes per day, and (3) passive smokers, non-smokers who are exposed to smokers at work and/or reside with at least one heavy smoker. The oxidant status of each individual is determined by measuring the isoprostane levels in urine and plasma. Isoprostanes are known to increase dramatically under conditions of oxidative stress (Roberts, L. J., et al., Free Radical Biology and Medicine 28, 505–513 (2000)). It is necessary to know the oxidant stress status of the individuals as lipid peroxidation is known to produce many VOCs, including alkanes, alkenes, alcohols, aldehydes, and ketones (Frankel, E. N., Lipid Oxidation; Oily Press: Dundee (1998)).

Breath compounds that correlate with the exposure categories and the isoprostane measurements are searched. Statistical algorithms, such as forward stepwise discriminant analysis (Phillips, M., et al., "Volatile organic compounds in breath as markers of lung cancer: a cross-sectional study, Lancet, 353, 1930–1933 (1999)), are used to identify the VOCs that are the best markers of exposure.

A diverse pool of individuals is obtained. It may be necessary to travel to selected locations to further promote the study. Interested individuals are provided with information regarding the procedures to be employed. After obtaining informed participants are asked to complete a questionnaire. Each questionnaire includes a cover page requesting the name and telephone number of the respondent that can be conveniently removed after coding. The questionnaire is a modified form of one which has been used for over 20 years by the Oakland University's Meadow Brook Health Enhancement Institute. Each questionnaire solicits information regarding age, sex, race, and medical history. It also solicits information regarding dietary habits, exercise regimen, smoking history, average number of cigarettes smoked per day, passive smoking, alcohol consumption, and medications taken (including antioxidant vitamins). Volunteers are paid for their initial responses.

Participants are selected based on questionnaire responses. The goal is to assemble a diverse distribution of age and sex matched participants. Volunteers selected for further participation in this study are contacted by telephone and scheduled for specimen collection. They are reminded of the purpose of the study and their right to withdraw at anytime. Individuals expecting to continue are instructed to refrain from eating or smoking for 12 hours prior to sample collection. The questionnaire responses are evaluated by designating three levels (low, medium, high) for several parameters, including smoking, exercise, anti-oxidant vitamin supplementation, and age. These parameters are then assigned a letter code, and the levels for each parameter code transferred to a table containing randomly assigned donor codes. After encoding, the cover sheet of the questionnaires, containing the names of volunteers, are removed and destroyed. Sample donors will be paid $25.

Breath: Volunteers are fitted with a nose clip and instructed to breathe into the breath collection apparatus for 5 minutes. 10 L of alveolar breath VOCs is collected on a sorbent tube. A room air sample is collected simultaneously on a second sorbent tube. Upon completion of breath sampling, each tube is placed in a labeled, hermetically-sealed container. The GC×2GC system is used to analyze the breath and air samples. An internal standard is added to each tube. Each chromatographic peak is integrated and tabulated. The alveolar gradient of each compound is calculated by subtracting the relative peak area of the room air sample from the relative peak area of the breath sample. The concentrations of selected compounds are determined from standard calibration curves.

Blood: 50 cc of peripheral blood is obtained by venipuncture into a Vacutainer containing EDTA as an anticoagulant, with precautions to avoid transmission of blood borne pathogens. Following low speed centrifugation, the plasma is separated and aliquoted. A known quantity of isoprostane is added to two fractions (spiked samples) to control for potential losses during extraction. Aliquots of blood is treated with 5 mg lipase obtained from the yeast, *Candida cylindraccae,* at 37° C. for 1 hr to hydrolyze esterified isoprostanes. Multiple coded aliquots are then frozen at −80° C. for subsequent analyses. This minimizes differences in isoprostane levels that can result from ex vivo peroxidation in plasma samples. The levels of free and total isoprostanes are determined using the OBR commercial ELISA kit.

Urine: Participants donate a urine sample during their visit to the collection facility. The sample is marked with a coded label. To normalize for variations in urinary output, creatinine levels in urine is measured using a calorimetric procedure described previously (19). Urinary cotinine is also measured using a standard calorimetric method (20) to provide a quantitative measure of nicotine metabolism and to confirm levels of smoking reported on questionnaires. The levels of free and total isoprostanes are determined using the OBR commercial ELISA kit. The results are normalized to the creatinine level.

The dual secondary columns can be fed by other standard switching means such as thermal modulation of the sample. Obviously there can be more than two secondary columns which are fed from a common source. All of these variations will produce the improved resolution and compound resolution of the present invention.

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

In claim:

1. A method for comprehensive two-dimensional gas chromatography comprising the steps of;
   injecting a sample into a primary column to obtain a first dimension;
   communicating said sample from said primary column through a valve which accumulates the sample;
   injecting at least a portion of said accumulated sample from said valve through a single connection to the valve simultaneously into a first and a second secondary column to obtain pair of second dimensions and wherein the first secondary column has a selectivity different from the second secondary column.

2. The method of claim 1 wherein the primary column has a first flow capacity smaller than a combined second and third flow capacities of the secondary columns and wherein the valve accumulates the sample for transfer to the secondary columns through the Y connection.

3. The method of claim 2 wherein the ratio of second and third flow capacities to the first flow capacity is about 26.6 to 1.

4. The method of claim 1 wherein the single connection is through a Y connection with two arms connected to the secondary columns and a leg connected to the valve.

5. A comprehensive two-dimensional gas chromatograph apparatus, said apparatus comprising:
   a primary column, said primary column interacting with a sample to provide a first dimension result;
   a first secondary column and a second secondary column, said sample interacting with each of said first and second secondary columns to provide a pair of second dimension results; and
   a valve, said valve providing fluid communication of said sample from said primary column simultaneously to each said first and second secondary columns by accumulation of the sample in the valve and then transfer into the secondary columns, whereby said secondary columns are in a parallel arrangement through a single connection to the valve and wherein the first secondary column has a selectivity different from the second secondary column.

6. The apparatus of claim 5, wherein said primary column is nonpolar.

7. The apparatus of claim 5, wherein said first and said second secondary columns are polar.

8. The apparatus of claim 5 wherein the single connection is through a Y connection with two arms connected to the secondary columns and a leg connected to the valve.

9. A comprehensive two-dimensional gas chromatograph apparatus, said apparatus comprising:
   a primary non-polar column, said primary column interacting with sample to provide a first dimension result;
   a first polar secondary column and a second polar secondary column, said sample interacting with each of said first and second secondary columns to provide a pair of second dimension results; and a valve, said valve providing fluid communication of said sample from said primary column to each said first and second secondary columns by accumulation of the sample in the valve and simultaneous periodic injection from the valve into the secondary columns, whereby said secondary columns are in a parallel arrangement through a single connection to the valve and wherein the first secondary column has a selectivity different from the second secondary column.

10. The apparatus of claim 9 wherein the primary column has a first flow capacity smaller than a combined second and third flow capacities of the secondary columns and wherein the valve accumulates the sample for transfer to the secondary columns through the single connection to the valve.

11. The apparatus of claim 10 wherein the ratio of second and third flow capacities to the first flow capacity is about 26.6 to 1.

12. The apparatus of claim 9 wherein the single connection is through a Y connection with two arms connected to the secondary columns and a leg connected to the valve.

* * * * *

UNITED STATES PATENT AND TRADEMARK OFFICE
CERTIFICATE OF CORRECTION

PATENT NO.   : 6,632,268 B2
DATED        : October 14, 2003
INVENTOR(S)  : John V. Seeley It is certified that error appears in the above-identified patent and that said Letters Patent is hereby corrected as shown below:

Column 6,
Line 48, "0.4 mm" should be -- 0.4 min --.
Line 55, "DE-Wax" should be -- DB-Wax --.

Column 13,
Line 62, "1.00 mm" should be -- 1.00 min --.

Column 14,
Line 1, "5 in" should be -- 5 m --.
Line 8, "5-port" should be -- 6-port --.

Signed and Sealed this

Twenty-second Day of June, 2004

JON W. DUDAS
*Acting Director of the United States Patent and Trademark Office*